United States Patent [19]
Nikiforov et al.

[11] Patent Number: 5,964,995
[45] Date of Patent: Oct. 12, 1999

[54] METHODS AND SYSTEMS FOR ENHANCED FLUID TRANSPORT

[75] Inventors: Theo T. Nikiforov, Campbell; Sang Jeong, San Francisco, both of Calif.

[73] Assignee: Caliper Technologies Corp., Mountain View, Calif.

[21] Appl. No.: 08/833,279

[22] Filed: Apr. 4, 1997

[51] Int. Cl.⁶ .................................................. G01N 27/26
[52] U.S. Cl. ............................................ 204/450; 204/454
[58] Field of Search .................................. 204/450–455, 204/601–605

[56] References Cited

U.S. PATENT DOCUMENTS

| | | | |
|---|---|---|---|
| 4,675,300 | 6/1987 | Zare | 436/172 |
| 4,908,112 | 3/1990 | Pace | 204/299 |
| 5,096,554 | 3/1992 | Chin | 204/180 |
| 5,110,424 | 5/1992 | Chin | 204/180 |
| 5,181,999 | 1/1993 | Wiktorowicz . | |
| 5,192,405 | 3/1993 | Petersen | 204/180 |
| 5,264,101 | 11/1993 | Demorest | 204/299 |
| 5,391,274 | 2/1995 | Shieh | 204/180.1 |
| 5,415,747 | 5/1995 | Holloway | 204/180.1 |
| 5,578,179 | 11/1996 | Demorest et al. | 204/451 |
| 5,585,069 | 12/1996 | Zanzucchi et al. | 422/100 |
| 5,632,876 | 5/1997 | Zanzucchi et al. | 204/600 |
| 5,660,701 | 8/1997 | Grushka | 204/451 |
| 5,779,868 | 7/1998 | Parce et al. | 204/604 |
| 5,800,690 | 9/1998 | Chow et al. | 204/450 |

FOREIGN PATENT DOCUMENTS

| | | |
|---|---|---|
| WO 96/04547 | 2/1996 | WIPO . |
| WO 97/02357 | 1/1997 | WIPO . |
| WO 98/10273 | 3/1998 | WIPO . |

OTHER PUBLICATIONS

Bao et al., "Ultramicro Enzyme Assays in Capillary Electrophoretic System," *J. Chromatog.* 608:217–224 (1992).

Dasgupta et al., "Electroosmosis: A Reliable Fluid Propulsion System for Flow Injection Analysis," *Anal. Chem.* 66:1792–1798 (1994).

Manz et al., "Electroosmotic Pumping and Electrophoretic Serparations for Miniaturized Chemical Analysis Systems," *J. Michromech. Microeng.* 4:257–265 (1994).

Ramsey et al., "Microfabricated Chemical Measurement Systems," *Nature Med.* 1 (10):1093 (1995).

Seiler et al., "Planar Glass Chips for Capillary Electrophoresis: Repetitive Sample Injection, Quantitation and Separation Efficiency," *Anal. Chem.* 65:1481–1488 (1993).

Seiler et al., "Electroosmotic Pumping and Valveless Control of Fluid Flow within a Manifold of Capillaries on a Glass Chip," *Anal. Chem.* 66:3485–3491 (1994).

*Primary Examiner*—Robert Warden
*Assistant Examiner*—Andrew Aldag
*Attorney, Agent, or Firm*—Matthew B. Murphy

[57] ABSTRACT

The present invention generally provides methods for enhancing transport and direction of materials in fluidic systems, which systems utilize electroosmotic (E/O) flow systems, to affect that transport and direction. The methods generally comprise providing an effective concentration of at least one zwitterionic compound in the fluid containing the material that is to be transported or directed.

20 Claims, 4 Drawing Sheets

E/O Flow

| Y- Y-<br>Y- Y- | | X+ B- X+ B-<br>X+ B- X+ B- | | A-<br>A- A-<br>A- A- |
|---|---|---|---|---|

METHODS AND SYSTEMS FOR ENHANCED FLUID TRANSPORT

BACKGROUND OF THE INVENTION

There has been a growing interest in the development and manufacturing of microscale fluid systems for the acquisition of chemical and biochemical information, in both preparative and analytical capacities. Adaptation of technologies from the electronics industry, such as photolithography, wet chemical etching and the like, has helped to fuel this growing interest.

One of the first areas in which microscale fluid systems have been used for chemical or biochemical analysis was in the area of capillary electrophoresis (CE). CE systems generally employ fused silica capillaries, or more recently, etched channels in planar silica substrates, filled with an appropriate separation matrix or medium. A sample fluid that is to be analyzed is injected at one end of the capillary or channel. Application of a voltage across the capillary then permits the electrophoretic migration of the species within the sample. Differential electrophoretic mobilities of the constituent elements of a sample fluid, e.g., due to their differential net charge or size, permits their separation, identification and analysis. In order to optimize the separation aspect of the CE applications, researchers have sought to maximize the electrophoretic mobility of charged species relative to each other and relative to the flow of the fluid through the capillary resulting from, e.g., electroosmosis. See, e.g., U.S. Pat. No. 5,015,350, to Wiktorowicz, and U.S. Pat. No. 5,192,405 to Petersen et al.

In comparison to these CE applications, the technologies of the electronics industry have also been focused on the production of small scale fluidic systems for the transportation of small volumes of fluids over relatively small areas, to perform one or more preparative or analytical manipulations on that fluid. These non-CE fluidic systems differ from the CE systems in that their goal is not the electrophoretic separation of constituents of a sample or fluid, but is instead directed to the bulk transport of fluids and the materials contained in those fluids. Typically, these non-CE fluidic systems have relied upon mechanical fluid direction and transport systems, e.g., miniature pumps and valves, to affect material transport from one location to another. See, e.g., Published PCT Application No. 97/02357. Such mechanical systems, however, can be extremely difficult and expensive to produce, and still fail to provide accurate fluidic control over volumes that are substantially below the microliter range.

Electroosmotic (E/O) flow systems have been described which provide a substantial improvement over these mechanical systems, see, e.g., Published PCT Application No. WO 96/04547 to Ramsey et al. Typically, such systems function by applying a voltage across a fluid filled channel, the surface or walls of which have charged or ionizeable functional groups associated therewith, to produce electroosmotic flow of that fluid in the direction of the current. Despite the substantial improvements offered by these electroosmotic fluid direction systems, there remains ample room for improvement in the application of these technologies. The present invention meets these and other needs.

SUMMARY OF THE INVENTION

The present invention generally provides methods, systems and devices which provide for enhanced transportation and direction of materials using electroosmotic flow of a fluid containing those materials. For example, in a first aspect, the present invention provides methods of enhancing material direction and transport by electroosmotic flow of a fluid containing that material, which method comprises providing an effective concentration of at least one zwitterionic compound in the fluid containing the material.

In a related aspect, the present invention also provides methods of reducing electrophoretic separation of differentially charged species in a microscale fluid column, where that fluid column has a voltage applied across it, which method comprises providing an effective concentration of at least one zwitterionic compound in the fluid.

The present invention also provides microfluidic systems which incorporate these enhanced fluid direction and transport methods, i.e., provide for such enhanced fluid transport and direction within a microscale fluid channel structure. In particular, these microfluidic systems typically include at least three ports disposed at the termini of at least two intersecting fluid channels capable of supporting electroosmotic flow. Typically, at least one of the intersecting channels has at least one cross-sectional dimension of from about 0.1 $\mu$m to about 500 $\mu$m. Each of the ports may include an electrode placed in electrical contact with it, and the system also includes a fluid disposed in the channels, whereby the fluid is in electrical contact with those electrodes, and wherein the fluid comprises an effective concentration of a zwitterionic compound.

BRIEF DESCRIPTION OF THE FIGURES

FIG. 1A illustrates an optimal scenario where differentially charged chemical species contained in discrete fluid volumes have apparent mobilities that are substantially the same as the electroosmotic flow rate for the fluid. FIG. 1B illustrates the situation wherein the apparent mobility of positively charged species is greater than the rate of electroosmotic flow and the apparent mobility of negatively charged species is less than or opposite to the rate of electroosmotic flow, resulting in the electrophoretic biasing of the charged species within the discrete fluid volumes. FIG. 1C illustrates the situation where the apparent mobilities of charged species are substantially different from the rate of electroosmotic flow of the fluid, such that the charged species in the two discrete fluid volumes overlap.

DETAILED DESCRIPTION OF THE INVENTION

I. General

Figure 1A:
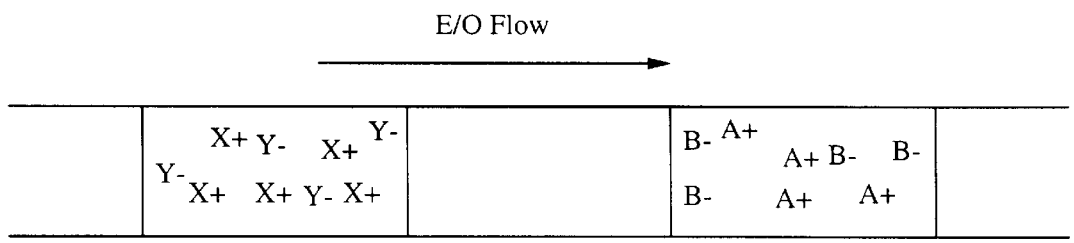
FIGS. 1a–1c are a schematic illustration of the effects of electrophoretic mobility of charged species on the migration of those species in a coherent electroosmotic fluid flow.

The present invention generally provides methods and systems for the enhanced transportation and direction of materials within fluidic systems, which utilizes the electroosmotic flow of fluids containing those materials. By "enhanced transportation and direction" is generally meant the electroosmotic flow and direction of fluids within fluidic systems, which shows: (1) a reduction in the electrophoretic mobility of a charged species relative to the electroosmotic flow of the fluid containing that charged species; and/or (2) an increase in the overall electroosmotic flow of that fluid, relative to such systems not incorporating the present invention, as described herein.

A. Reduction of Electrophoretic Mobility of Charaed Species

As noted previously, in capillary electrophoresis applications, the general goal is to maximize the separation between different species contained in a sample of interest, in order to separately analyze those species, identify their presence within the sample, or the like. This is accomplished by maximizing the differences in the electrophoretic mobilities of these species, which differences may result from differences in their size and/or net charge.

In the E/O fluid direction systems described herein, however, the goals are somewhat different from those of CE systems. In particular, the general object of these E/O fluid direction systems is the transport and/or direction of material of interest contained in a volume of fluid or multiple discrete volumes of fluid, from one location in the system to another, using controlled E/O flow. Because these fluids are generally to be subjected to further manipulation or combination with other fluids, it is generally desirable to affect the transportation of these fluids without substantially altering their make-up, i.e., electrophoretically separating or biasing differentially charged or sized materials contained within those fluids.

Similarly, where these systems are being used to serially transport small volumes of fluids or multiple discrete volumes of different fluids along the same channels, it is generally desirable to transport these fluid volumes as coherently as possible, i.e., minimizing smearing of materials or diffusion of fluids. In particular, because these systems are preferably utilized in microfluidic applications, the improved coherency of a particular fluid volume within the E/O flow system permits the transport of larger numbers of different fluid volumes per unit time. Specifically, maintaining higher fluid volume coherency allows separate volumes to be transported closer together through the channels of the system, without resulting in excessive intermixing of these volumes. Further, maintenance of maximum fluid volume coherency during the transport and direction of the fluids permits more precise control of volumetric delivery of materials within these systems.

Despite the differing goals of the CE systems and the E/O flow systems used in the present invention, in each case, the application of an electrical field across a fluid of interest has the same basic result. Specifically, where the fluid of interest comprises charged species, or is made up of a plurality of differentially charged chemical species, application of a voltage across that fluid, e.g., to obtain E/O flow, will result in those charged species electrophoresing within the fluid, and the differentially charged species electrophoresing at different rates. As such, in a channel having a negative surface potential, negatively charged species will have an electrophoretic mobility opposite to the direction of E/O flow, whereas positively charged species will have an electrophoretic mobility in the same direction of E/O flow. The greater the number of charges a particular species has, the greater its electrophoretic mobility in the same or opposite direction of E/O flow. In systems employing electroosmotic fluid direction, this results in a net separation of differentially charged species that are contained within the fluid that is being transported.

Where one is transporting a particular volume of a given sample fluid, this separation can result in an electrophoretic biasing of the sample, where the positively charged species have a greater apparent mobility, than negatively charged species. "Apparent mobility" as used herein, generally refers to the overall mobility of a given species within the fluidic system. in the systems of the present invention, apparent mobility is typically defined as the rate of E/O mobility plus the electrophoretic mobility. Where electrophoretic mobility is opposite to the direction of E/O flow, i.e., negative, this leads to an apparent mobility that is less than the E/O mobility.

In the case of species having high electrophoretic mobility, e.g., highly charged species, the effect can be magnified to the point that the apparent mobility of such species is substantially different from the E/O mobility of the fluid containing them. For example, species possessing multiple negative charges may have an electrophoretic mobility substantially opposite the direction of E/O mobility, resulting in a substantial reduction in the apparent mobility of that species. Where that reduction is sufficiently large, it can result in that species being effectively "left behind" by the particular volume of fluid that is being transported.

Conversely, a species bearing multiple positive charges may have an apparent mobility that is far greater than that of the fluid being transported and other species contained therein, such that the species is transported well ahead of the fluid volume.

This problem is not as significant where one is transporting large volumes of fluid from one location to another. Specifically, one can reduce the effects of the electrophoretic separation of a fluid by collecting larger volumes, thereby reducing the contribution that biased portions of the fluid have on the overall fluid delivered.

However, the problem is substantially magnified when one wishes to transport a relatively small volume, or multiple small volumes of the same or different fluids, without separating the materials contained in the individual fluid volumes or intermixing the materials contained in separate volumes. Specifically, in transporting a one or a series of discrete volumes of a particular fluid or fluids, e.g., samples, test compounds, various elements of a screening system, species that have apparent mobilities that are substantially different from the E/O mobility of the particular fluid volume will travel ahead of, and behind the fluid volume, effectively smearing the materials that are sought to be delivered. As described above, this is a significant disadvantage where relatively precise fluid control is desired, or where smaller effective volumes are used. For example, where one is screening for compounds which affect a particular reaction mix, e.g., a biochemical system, it is generally desirable to be able to mix the elements necessary for that screen, e.g., enzyme, substrate and test inhibitor, and allow those elements to incubate together while transporting them to the ultimate detection area. Where those elements separate based upon their differential electrophoretic mobilites, this can have substantial adverse effects on the overall efficacy of the screening system.

More importantly, where a species in a first volume being transported has an apparent mobility that is substantially less than the E/O mobility of the fluid, while a species in a second or following volume has an apparent mobility that is substantially greater than the E/O mobility of the fluid that is being delivered, those two species can overlap within the flow system.

Figure 1B:
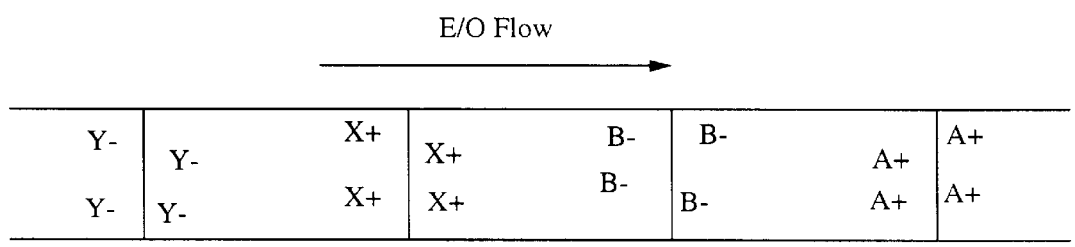
Figure 1C:
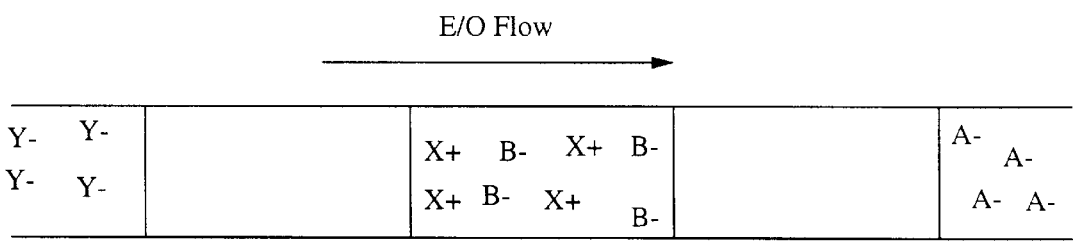

The above described problems are schematically illustrated in FIG. 1. FIG. 1A shows an optimal situation where discrete volumes or regions of fluids in a channel (fluids AB and XY, shown underlined) contain differentially charged species, e.g., X+ and Y−, and A+ and B−. In this optimal situation, these differentially charged chemical species have an apparent mobility that is not substantially different from the E/O mobility of the fluid containing those species. As a result, the various species are maintained substantially within their separate fluid regions. FIG. 1B illustrates the smearing effect which results when charged species, as a result of their greater electrophoretic mobilities, begin to migrate outside of their respective fluid volumes or regions. This results in a smearing of the materials that are being transported and substantially reduces the precision with which these materials can be transported. Finally, FIG. 1C illustrates the situation where the apparent mobility of the charged species is so substantially different from the E/O mobility of the fluid regions, that it results in the overlapping and intermixing of differentially charged species from different fluid regions. The intermixing of separate fluid volumes creates substantial problems where the fluid system is being used in the serial transport of multiple different fluids, e.g., as described in U.S. patent application Ser. No. 08/761,575, filed Dec. 6, 1996, and incorporated herein by reference in its entirety for all purposes.

Methods have been developed to prevent and/or correct for the excessive electrophoretic mobility of charged species, when those species are being transported in E/O fluid direction systems, by incorporating fluid barriers around the fluid being transported, in which the electrophoretic mobility of these charged species is substantially reduced, see, e.g., commonly assigned U.S. patent application Ser. No. 08/760,446, filed Dec. 6, 1996 (now U.S. Pat. No. 5,880,071), and incorporated herein by reference in its entirety for all purposes.

Generally, the enhanced E/O material transport and direction produced by the present invention is carried out by providing within the fluid component of the system, a compound or compounds that are capable of reducing the effects such an E/O system has on charged species contained within the fluid. For example, incorporation of these compounds within the fluid component of the E/O flow system typically results in a reduction in the electrophoretic mobility of charged species, and thus, reduces the differential electrophoretic mobility and apparent mobility of differentially charged species.

In preferred aspects, zwitterionic compounds or combinations thereof, are used to reduce the electrophoretic mobility of materials that are contained within the fluids that are sought to be transported using these E/O fluid direction systems, thereby achieving or substantially achieving the optimal situation shown in FIG. 1A.

Without being bound to a particular theory of operation, it is believed that such zwitterionic compounds interact with the charged species in a layer-like complex. The "complex" has the same net charge as the charged species, but that charge is spread over a much larger structure effectively reducing the charge:size ratio, and reducing the electrophoretic mobility of the complex. Because zwitterions are dipolar molecules, they can be effectively employed with respect to positively or negatively charged species.

While other methods can be used to effectively reduce the charge:size ratio of compounds in an E/O fluid direction system, these methods have numerous associated problems. For example, raising or lowering pH of the fluid containing the species can effectively reduce the level of charge of a chemical species by protonating or deprotonating functional groups present therein. While effective in reducing net charge of a given species, this method can have substantial adverse effects. Specifically, where the fluidic system is being utilized in the analysis of biological systems, e.g., enzymatic reactions, receptor/ligand interactions, or in transporting other materials sensitive to extremes of pH, the substantial variation of pH, e.g., from neutral or physiological conditions, can place the system well outside the optimal pH for subsequent manipulation or analysis. In some cases, the optimal pH for reducing the net charge of a particular species may denature or otherwise degrade active components of the materials that are being transported.

The incorporation of zwitterionic compounds as described herein, on the other hand, is readily compatible with systems to be used for the transport of pH sensitive materials, e.g., systems used in analysis of biological systems. In particular, different zwitterionic compounds, i.e., having different pI, may be selected depending upon the pH sensitivity of the material being transported. Accordingly, as can be readily appreciated from the foregoing, the present invention is particularly useful in E/O fluid direction systems where the materials to be transported include biological material, such as enzymes, substrates, ligands, receptors, or other elements of biological or biochemical systems, e.g., as those systems are defined in U.S. patent application Ser. No. 08/761,575, previously incorporated herein by reference for all purposes.

Another method that can be used to affect the charge:size ratio of a charged molecule of interest in an E/O fluid direction system involves interacting that charged molecule of interest with another molecule or species such that the two molecules form a complex having a different charge:size ratio. Merely by way of example, fluorescein is a molecule that carries two negative charges above neutral pH. The electrophoretic mobility of this molecule can be readily altered by adding an antibody, such as anti-fluorescein to the solution. The resulting complex will have a substantially reduced electrophoretic mobility over that of fluorescein alone. Again, while this method is effective, it too carries a number of disadvantages. First, because one must identify a compound that associates with the charged molecule of interest, a specifically associating compound must be identified for each charged molecular species in the fluid, and for each different fluid used in the system. Further, as is the case with the fluorescein/anti-fluorescein complex described above, incorporation of an active molecule into a larger complex can have an adverse effect desired activity or function of that molecule, i.e., substantially reduced fluorescence.

The methods and systems of the present invention, on the other hand do not have these associated problems. For example, the function of zwitterionic compounds in reducing electrophoretic mobility of charged species is generally applicable, i.e., does not require a specific interaction between the charged species and the zwitterion. Further, the nature of this interaction results in little or no effect on the properties of the charged molecule of interest.

B. Increase In E/O Mobility

In addition to the advantages of reducing the electrophoretic mobility of charged species within fluids that are being transported using E/O fluid directions systems, incorporation of zwitterionic compounds in many systems can also have the effect of increasing the E/O mobility in the fluid direction system, thereby further optimizing the apparent mobility of the material that is being transported.

In particular, incorporation of zwitterionic compounds within fluids being transported in E/O fluid direction systems has been shown to increase E/O mobility of those fluids. This effect is particularly apparent where those fluids include a protein component or other larger charged molecular species.

II. Compounds Useful in Practicing the Invention

A wide variety of zwitterionic and related chemical compounds may be employed according to the present invention. For example, such compounds include, e.g., betaine, sulfobetaine, taurine, aminomethane sulfonic acid, zwitterionic amino acids, such as glycine, alanine, β-alanine, etc., and other zwitterionic compounds such as HEPES, MES, CAPS, tricine and the like. In particularly preferred aspects, non-detergent, low molecular weight sulfobetaines are used in the methods of the present invention, such as dimethylethylaminopropane sulfonic acid, dimethylbenzylaminopropane sulfonic acid, and 3-(N-pyridinium)propane sulfonic acid.

Although generally described in terms of single species of zwitterionic compounds, it will be readily appreciated that the present invention also comprehends the use of combinations of the above described compounds. Such combinations can be readily tailored to optimize the effects seen on the overall fluidic system, as well as for their compatibility with the various components of the system, e.g., buffers, enzymes, substrates, receptors, ligands, test compounds, and the like.

Generally, the concentration of zwitterionic compounds within the fluids contained in the system, may be varied depending upon the effect desired, where lower concentrations yield less of an effect in reducing electrophoretic mobilities of materials contained within the fluid. Further, these effects may also be varied depending upon the nature of the charged species contained within the material of interest. Therefore, as used herein, the term "effective concentration" refers to a concentration of zwitterionic compounds that is sufficient to achieve a desired effect, and particularly, achieve some reduction in the electrophoretic mobility of a charged species of interest. Further, by "concentration" of zwitterionic compounds in the fluid" is meant the amount of such compounds added per unit volume, regardless of any subsequent conversion of such compounds within the fluid system. Typically, however, effective concentrations of zwitterionic compounds will preferably be greater than about 5 mM, typically greater than about 10 mM, and often greater than about 50 mM. Although zwitterionic compounds may generally be present at levels approaching their solubility limits in practicing the present invention, preferred concentrations of the zwitterionic compounds in the fluid that is sought to be transported within the system will range between about 1 mM and 2 M and more preferably between about 5 mM and 2 M.

III. Application to Microfluidic Systems

As noted previously, the present invention finds particular utility in fluidic systems that employ E/O fluid direction systems, and more particularly, microscale fluidic systems. By "E/O fluid direction systems" is generally meant fluidic systems that are made up of fluid channels or passages, chambers, ports or the like, wherein the movement of fluid within the systems, i.e., through the channels, or from one channel to another channel, or from one chamber to another chamber, is selectively directed through the controlled electroosmotic flow of that fluid. Examples of such controlled E/O flow systems are described in, e.g., Published PCT Application No. WO 96/04547, and commonly owned U.S. patent application Ser. Nos. 08/761,575 and 08/760,446 (now U.S. Pat. No. 5,880,071), each of which was previously incorporated herein by reference.

In preferred aspects, such fluid direction systems direct a fluid of interest through intersecting channel structures by applying a voltage gradient along the desired path of fluid flow. Voltages are typically simultaneously applied along the intersecting fluid paths, in order to propagate a containing or directing fluid flow, i.e., to contain or direct the fluid of interest along the desired path. For example, where the fluid of interest is being flowed along a first channel that is intersected by second channel, the flow of the fluid of interest is maintained within the first channel, i.e., prevented from diffusing into the intersecting channel, by simultaneously flowing fluid into the first channel from each side of the intersecting channel. This is generally done by simultaneously applying a voltage from the originating end to the terminating end of the first channel, and to each end of the intersecting channel, whereby appropriate E/O flow is obtained. As can be appreciated, this results in a fluid flow pattern in the first channel that appears "pinched." In another example, a fluid of interest may be directed from a first arm of a first channel into a first arm of an intersecting channel, by applying a voltage across the desired fluid flow path to generate fluid flow in that direction. In order to control fluid flow at the intersection, a containing fluid flow is generated along the entire length of the intersecting channel creating what is termed a "gated" flow. The fluid of interest can then be metered out or dispensed in a controlled fashion, into the remaining arm of the first channel by actively modulating the voltage to allow the fluid to flow into that arm, while preventing diffusion. Effectively, this results in a valving system without the necessity of mechanical elements. Finally, by modulating the rate of flow of the fluid of interest through an intersection as compared to the flow of diluents flowing in from the intersecting channels, these systems can be used as diluters.

By "microscale fluidic systems" is typically meant fluid systems that comprise reservoirs, conduits or channels, and/or chambers, wherein at least one cross sectional dimension, e.g., depth, width or diameter, of a particular fluid channel and/or chamber is in the range of from about 1 μm to about 500 μm, inclusive. Such microscale fluidic systems range from simple capillary systems, e.g., that employ a single fused silica capillary for delivering a particular fluid or fluids from a reservoir at one end of the capillary to the other end of the capillary, for analysis, combination with other reagents, and the like, to more complex integrated multichannel microfluidic devices fabricated in solid substrates, such as those described in U.S. patent application Ser. No. 08/761,575, previously incorporated herein by reference in its entirety for all purposes. In preferred aspects, the microscale fluidic system will employ at least one channel, and more preferably at least two intersecting channels which have at least one cross sectional dimension in the range from 1 μm to about 500 μm, and more preferably between about 1 μm and 100 μm.

The combination of these microscale dimensions with the relatively precise fluid control, described above, permits the controlled, repeatable direction or dispensing of extremely small volumes of fluid, which volumes are dictated by the volumes of the channels and/or intersections, e.g., a sample plug at an intersection, or by the timing of fluid flow, e.g., the amount of time or length of a fluid plug injected into a channel using gated flow.

Typically, the microfluidic systems employed in practicing the present invention will comprise a solid substrate that has the channels and/or chambers of the microfluidic system disposed within it. Substrates may be prepared from a number of different materials. For example, techniques employed in the fabrication of small scale fluidic devices are often derived from the electronics industry. As a result, substrate materials are often selected for compatibility with these manufacturing techniques, such as silica, silicon, gallium arsenide and the like. Typically, however, semiconducting materials are not preferred for practicing the present invention, as they are not compatible with the application of electric fields through fluids, without some modification, e.g., application of an insulating layer. Accordingly, in one preferred aspect, silica substrates are preferred in practicing the present invention.

Other substrate materials may also be employed in the microfluidic systems of the invention, and may generally be selected for their compatibility with the conditions to which they will be exposed, both in manufacturing, e.g., compatibility with known manufacturing techniques, and operation, e.g., compatibility with full range of operating conditions, including wide ranges of salt, pH, compositions, and application of electric fields. Examples of such substrates include polymeric materials, with the provision that such materials, either on their own, or through modification of the surfaces that contact the fluids of the system are capable of propagating E/O flow.

Typically, the substrate will have a first surface, and will be generally planar in shape. The intersecting channels are typically fabricated into the surface of the substrate as grooves. As noted previously, the channels may be fabricated into the surface of the substrate using, e.g., photolithography, wet chemical etching, and other known microfabrication techniques. Generally, a cover layer is overlaid on the surface of the substrate to seal the grooves, forming fluid channels or passages.

The devices generally include a number of ports or reservoirs fabricated therein, which ports are in electrical contact, and typically in fluid communication, with the intersecting channels. These ports generally provide a point at which electrodes can be placed in contact with the fluids, for directing fluid flow. These ports also often provide a reservoir of fluids that are used in the device or system. As such, the different ports are typically placed in contact with the fluid channels on different sides of a given intersection of two channels. For ease of fabrication, such ports are typically placed in electrical contact with each of the free termini of the various channels fabricated into the device. By "free termini" or "free terminus" is meant a nonintersected terminus of a channel.

For ease of discussion, the microfluidic devices and systems are generally described in terms of two intersecting channels. However, it will be readily appreciated that such devices and systems may readily incorporate more complex channel structures of three, four, five, ten, twenty and more intersecting channels. Further, such devices and systems also include parallel channel structures where more than one main channel may be intersected by large numbers of cross channels.

As described above, the present invention generally relates to methods of enhancing electroosmotic flow, and particularly, application of these methods to microfluidic systems which utilize such E/O flow in the transport and direction of fluids within these systems. This is in contrast to capillary electrophoresis systems (CE) which seek to minimize E/O mobility of fluids, while maximizing differential electrophoretic mobility of species contained in these fluids. Often this is done by incorporating a separation matrix within the channels of the CE systems, which furthers these goals. Thus, the presently described systems are generally described in terms of channels which permit or are capable of free electroosmotic flow. By this is meant that the channels in which E/O flow is desired will generally have a sufficient surface potential for propagating E/O flow or mobility of fluids and materials in those channels. At the same time these channels are devoid of obstructions which might impede that flow, and particularly such channels will be free of any separation media or matrices.

The present invention is further illustrated with reference to the following non-limiting examples.

EXAMPLES

The efficacy of incorporating zwitterionic compounds for reducing electrophoretic mobility of charged species in E/O flow systems was demonstrated in a fused silica capillary, having 57 cm total length, 50 cm effective length and internal diameter of 75 $\mu$m. All samples were run in 50 mM HEPES buffer at pH 7.5. All of the running buffers were prepared fresh from concentrated stock solution. For each run, the samples were pressure injected into the capillary for 20 seconds, separated at 30 kV, and detected at 254 nm. Following each run, the capillary was rinsed with 1N NaOH for 2 minutes followed by a 5 minute rinse with replacement buffer.

The level of electroosmotic flow within the capillary was determined by incorporation of mesityl oxide (4 $\mu$l in 4 ml $H_2O$), a neutral detectable marker, while effects on electrophoretic mobility were determined by incorporation of 5.0 mM dFMUP (6,8-difluoro-4-methylumbelliferyl phosphate) in water, a detectable compound having two negative charges at neutral pH.

Example 1

Use of NDSB-195

The first experiment tested the effect of the zwitterionic compound 3-(N-ethyl-N,N-dimethylammonium) propanesulfonate) (NDSB-195) on electrophoretic mobility of charged species (dFMUP) within a buffer filled capillary, as well as on overall electroosmotic flow of that buffer within the capillary. The experiment was duplicated in the presence and absence of a protein component (0.1 mg/ml BSA).

Three different concentrations of NDSB-195 were tested: 0.1 M; 0.5 M; or 1.0 M final concentration, and compared to a negative control (no NDSB-195). For each run, the retention time of mesityl oxide and dFMUP was determined, and used to calculate the E/O mobility for the run ($\mu$EO), electrophoretic mobility ($\mu$EP) of the dFMUP, and the apparent mobility ($\mu$App) of the dFMUP ($\mu$App=$\mu$EO+$\mu$EP). The results are shown in Table I, below, as averages of triplicate runs:

TABLE I

| [NDSB] M | $\mu$EO × $10^{-4}$ (+BSA) | $\mu$EO × $10^{-4}$ (-BSA) | $\mu$App × $10^{-4}$ (+BSA) | $\mu$App × $10^{-4}$ (-BSA) | $\mu$EP × $10^{-4}$ (+BSA) | $\mu$EP × $10^{-4}$ (-BSA) |
|---|---|---|---|---|---|---|
| 0 | 2.94 | 4.77 | 0.20 | 2.02 | -2.74 | -2.75 |
| 0.10 | 4.31 | 5.42 | 1.54 | 2.87 | -2.78 | -2.55 |
| 0.50 | 5.74 | 5.59 | 3.49 | 3.34 | -2.24 | -2.24 |
| 1.00 | 5.68 | 5.20 | 3.60 | 3.28 | -2.08 | -1.92 |

Figure 2:
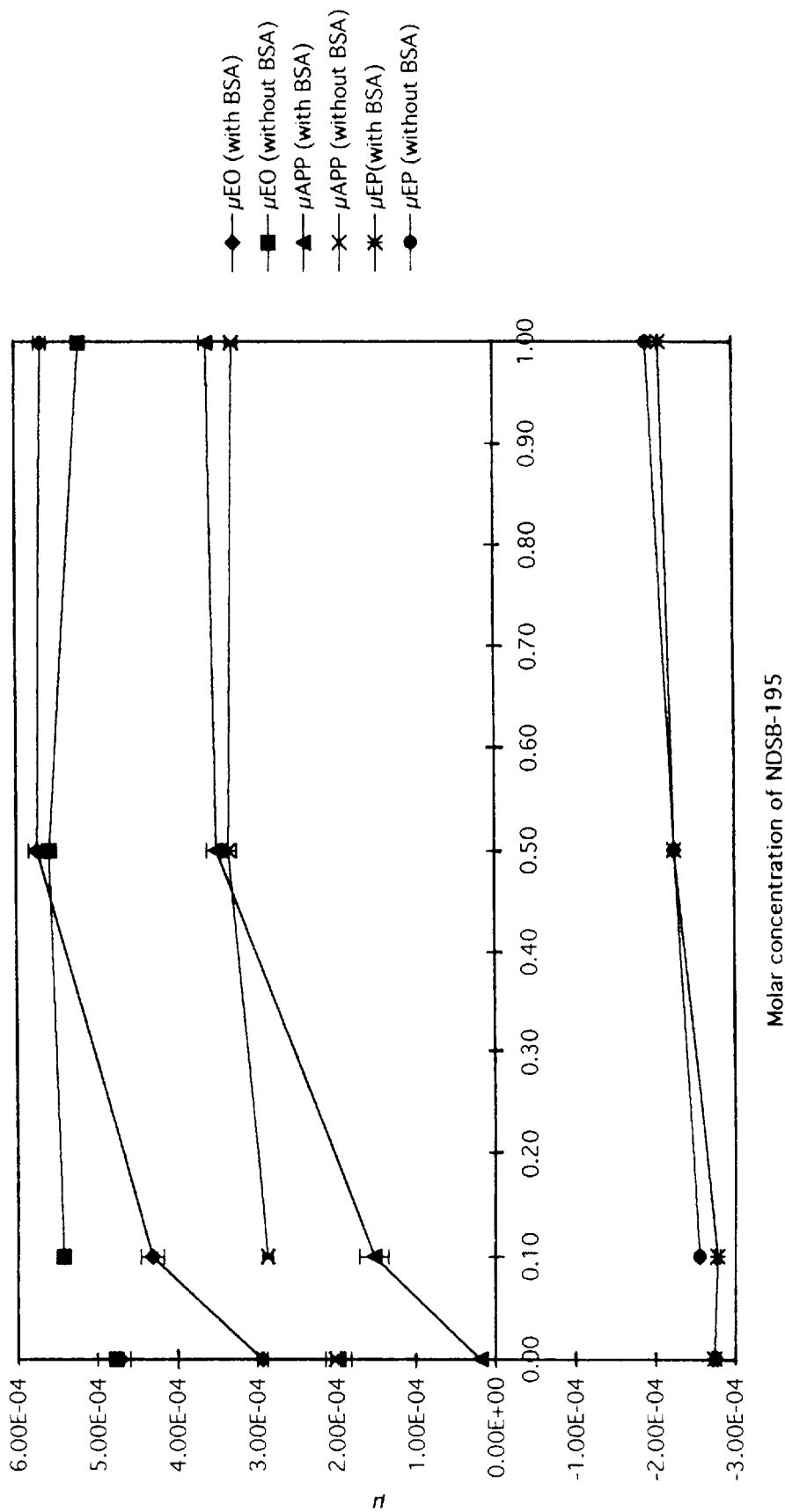
FIG. 2 is a graph showing the effect of the addition of sulfobetaine on electroosmotic flow and apparent mobility of charged species, under conditions of electroosmotic flow.

FIG. 2 shows a plot of E/O flow, electrophoretic mobility and apparent mobility of dFMUP, as a function of increasing concentration of NDSB-195, both in the presence and absence of BSA. The standard deviation is also shown for each point plotted. As is apparent from these data, inclusion of NDSB-195 substantially reduces the net electrophoretic mobility of DFMUP, both in the absence and presence of a protein component (BSA). In addition to reducing this electrophoretic mobility, the incorporation of NDSB also increases the E/O flow rate of the system. The net result is that the apparent mobility of the charged species is brought closer to the E/O flow rate of the system.

Example 2

Use of β-Alanine

A similar experiment was performed utilizing an amino acid, β-alanine, as the zwitterionic component. In particular, β-alanine was incorporated in the same system as described above, at two different concentrations, 0.50 M and 1.0 M, and compared to a negative control (containing no β-alanine), and in the presence and absence of a protein component. pH was not adjusted following addition of β-alanine. The results of this experiment are shown in Table II, below:

TABLE II

| Buffer | Analyte | R.T. | $\mu EO \times 10^{-4}$ | $\mu App. \times 10^{-4}$ | $\mu EP \times 10^{-4}$ |
|---|---|---|---|---|---|
| 50 mM HEPES, pH 7.5 | Mes. Ox. | 3.41 | 4.64 | 4.64 | |
| | dFMUP | 8.61 | | 1.84 | −2.80 |
| 50 mM HEPES, pH 7.5/BSA (0.1 mg/ml) | Mes. Ox. | 3.90 | 4.06 | 4.06 | |
| | dFMUP | 14.82 | | 1.07 | −2.99 |
| 50 mM HEPES, pH 7.5/BSA (0.1 mg/ml)/ 500 mM ala. | Mes. Ox. | 3.00 | 5.28 | 5.28 | |
| | dFMUP | 5.44 | | 2.91 | −2.37 |
| 50 mM HEPES, pH 7.5/500 mM ala. | Mes. Ox. | 3.00 | 5.28 | 5.28 | |
| | dFMUP | 5.51 | | 2.87 | −2.40 |
| 50 mM HEPES, pH 7.5/BSA (0.1 mg/ml)/ 500 mM ala. | Mes. Ox. | 2.94 | 5.39 | 5.39 | |
| | dFMUP | 4.94 | | 3.21 | −2.18 |
| 50 mM HEPES, pH 7.5/500 mM alanine | Mes. Ox. | 2.96 | 5.35 | 5.35 | |
| | dFMUP | 4.99 | | 3.17 | −2.18 |

R.T. = retention times (mins)

Again, incorporation of β-alanine results in a decrease in the electrophoretic mobility of the dFMUP, and a net increase in its apparent mobility.

Example 3

Concurrent Application to Differentially Charged Species.

Each of the above examples illustrates that the incorporation of zwitterionic compounds results in a reduction of the electrophoretic mobility of negatively charged species in the system (dFMUP). The following experiment illustrates the same efficacy in samples containing both positively and negatively charged chemical species.

This experiment tested the effect of 1 M NDSB on the electrophoretic mobility of a positively charged species (benzylamine) and a negatively charged species (benzoic acid) in the same capillary system described above. This experiment utilized two different buffer systems: 200 mM borate at pH 8.7; and 200 mM HEPES at pH 7.0. These experiments also incorporated dimethylformamide (DMF) as a neutral marker compound, for ascertaining E/O mobility.

Table 3, below, illustrates the effect of incorporation of the zwitterionic compound NDSB on the electrophoretic mobility and apparent mobility of both positively and negatively charged species.

TABLE III

| Buffer | Analyte | R.T. | $\mu EO \times 10^{-4}$ | $\mu APP \times 10^{-4}$ | $\mu EP \times 10^{-4}$ |
|---|---|---|---|---|---|
| 200 mM Borate pH 8.7 | DMF | 3.05 | 5.19 | 5.19 | — |
| | Benzylamine | 2.04 | — | 7.76 | 2.57 |
| | Benzoic Acid | 7.13 | — | 2.22 | −2.97 |
| 200 mM Borate pH 8.9, 1M NDSB | DMF | 3.26 | 4.86 | 4.86 | — |
| | Benzylamine | 2.47 | — | 6.41 | 1.55 |
| | Benzoic Acid | 5.43 | — | 2.92 | −1.94 |
| 200 mM HEPES pH 7.0 | DMF | 2.97 | 5.33 | 5.33 | — |
| | Benzylamine | 1.93 | — | 8.20 | 2.87 |
| | Benzoic Acid | 5.25 | — | 3.02 | −2.32 |
| 200 mM HEPES pH 7.0, 1M NDSB | DMF | 3.56 | 4.45 | 4.45 | — |
| | Benzylamine | 2.40 | — | 6.60 | 2.15 |
| | Benzoic Acid | 5.84 | — | 2.71 | −1.74 |

From these data, it is clear that incorporation of the zwitterionic compound NDSB in either buffer system reduced the electrophoretic mobility of both the positively charged species, benzylamine, and the negatively charged species, benzoic acid. Further, although in this system, NDSB resulted in a decrease in the E/O flow rate, there was nonetheless, a reduction in the difference between the E/O mobility and the apparent mobility for both of the differentially charged species, e.g., the apparent mobility of the positively charged species was reduced while the apparent mobility of the negatively charged species increased.

Example 4

Enzyme Inhibition in Presence and Absence of NDSB in Microfluidic System.

Figure 3:
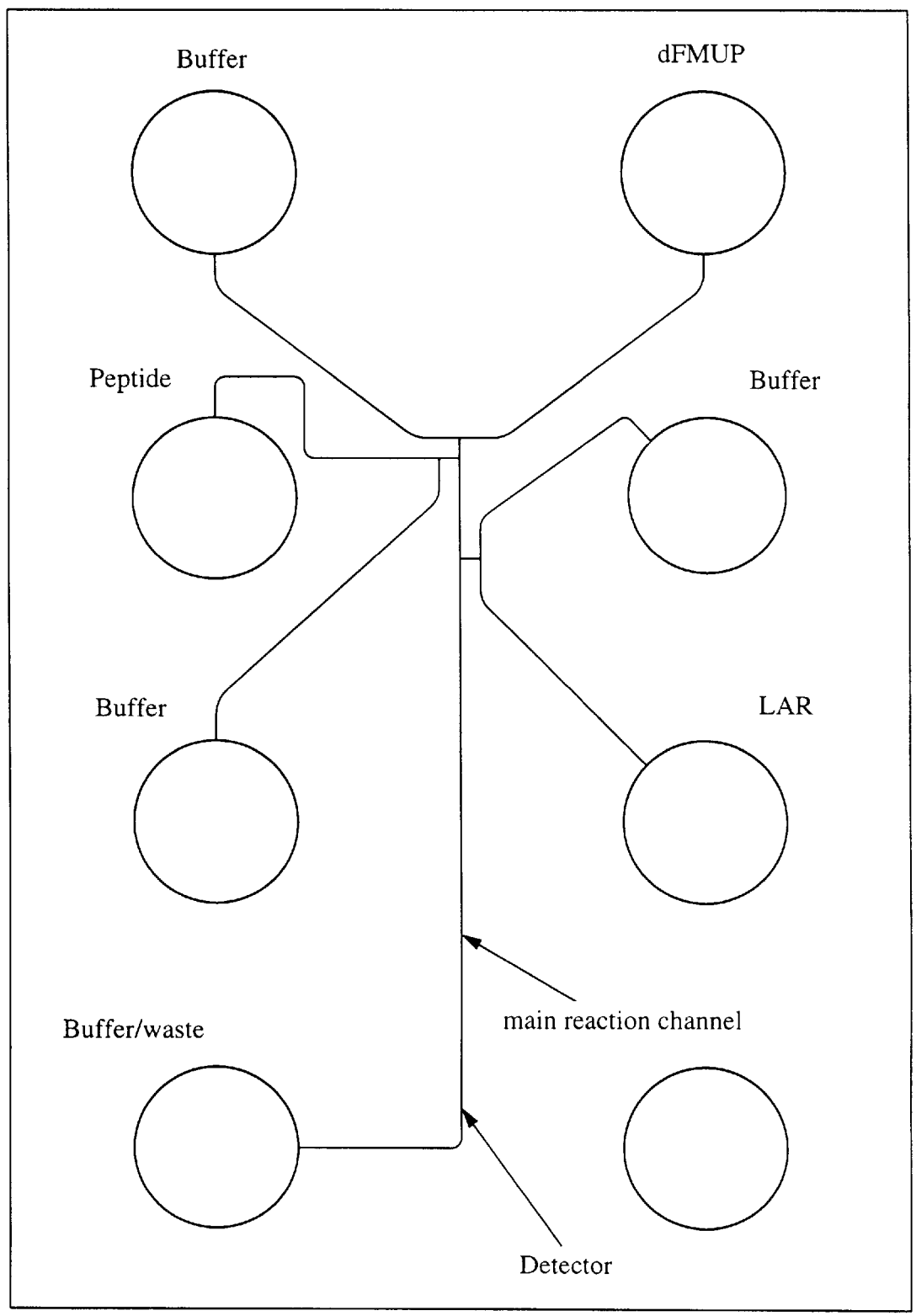
FIG. 3 illustrates a microfluidic device used to perform enzyme inhibitor assays.

An enzyme inhibition assay was performed using a microfluidic device having a well/channel structure as shown in FIG. 3. Standard semiconductor photolithographic techniques were used to etch channels 70 µm wide and 10 µm deep, in a 525 µm thick soda lime glass substrate, and a second 2 mm thick layer of glass having 3 mm diameter holes drilled through it, was thermally bonded to the first, providing the various wells.

All reagents were diluted in the same buffer solution which also served as the running buffer: 25 mM HEPES, pH 7.9, for the control; and 25 mM HEPES, 1 M NDSB-195 (non-detergent sulfobetaine, MW 195) (available from Calbiochem-Novabiochem, La Jolla, Calif.), pH 7.9, for the test run. The assay solutions were prepared from stock solutions of 5000 U/mg leukocyte antigen related phosphatase (LAR) (enzyme) (New England Biolabs, Beverly, Mass.), 10 mM dFMUP in water, a fluorogenic substrate for LAR (substrate)(available from Molecular Probes, Eugene, Oreg.), and 1.4 mM of a known competitive inhibitor of LAR (inhibitor).

Detection of fluorescence was carried out using a Nikon inverted Microscope Diaphot 200, with a Nikon P101 photometer controller, for epifluorescent detection. An Opti-Quip 1200-1500 50 W tungsten/halogen lamp coupled through a 10× microscope objective provided the light source. Excitation and emission wavelengths were selected with a DAPI filter cube (Chroma, Brattleboro Vt.) fitted with a DM400 dichroic mirror, 340–380 nm excitation filter and 435–485 nm barrier filter. Reagent well currents and voltages on the chip were controlled using a Caliper 3180 Chip Controller (Palo Alto, Calif.). The currents and voltages ranged +/−10 $\mu$A and 0–2000 V. Data was collected on a Macintosh Power PC 7200/120.

The channels of the device were filled with running buffer by placing the buffer in a buffer well and allowing capillary action to distribute the buffer throughout the channels. 125 nM LAR enzyme was placed in the enzyme well, 50 $\mu$M dFMUP was placed in the substrate well and 200 $\mu$M of a known competitive inhibitor of LAR was placed in the inhibitor well.

The assay was performed using the following injection cycle, with the indicated final reagent concentrations in the injection channel: (1) buffer; (2) substrate (17 $\mu$M); (3) buffer; (4) substrate+enzyme (83 nM); (5) buffer; and (6) substrate+inhibitor (66 $\mu$M)+enzyme. The total flux of reagents remained constant during each step of the assay by maintaining a constant overall sum of combined currents from the wells.

Figure 4:
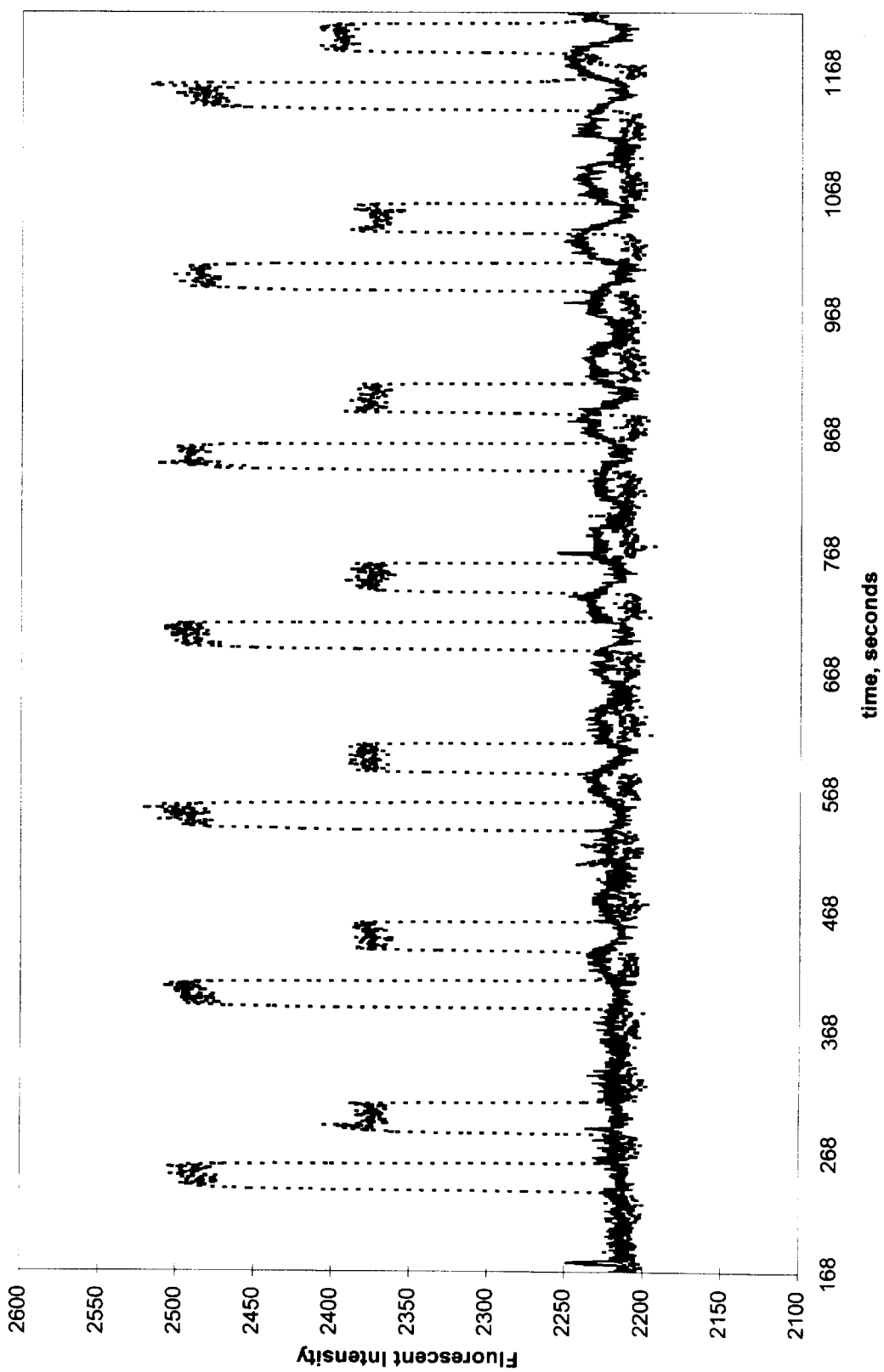
FIG. 4 illustrates a graphical comparison of enzyme inhibition assays in the presence and absence of a zwitterionic compound, NDSB.

The raw fluorescent data from this experiment are shown in FIG. 4. The control data, e.g., in the absence of NDSB-195, is shown as a gray line, running at or near the baseline of the data. As can be seen from this data, LAR action on the dFMUP substrate produces only a moderate signal, ranging between a fluorescent intensity of 2200 and 2250. Further, while some effect of the inhibitor is apparent through this assay at later time points, that effect is relatively small. Without being bound to a particular theory, it is believed that this is the result of two phenomena: (1) the LAR enzyme is interacting with the channel walls, resulting in a smearing of the enzyme throughout the assay, as indicated by the appearance of signal in the substrate only control; and (2) the high electrophoretic mobility of the dFMUP substrate opposite the electroosmotic mobility of the system results in the substrate and enzyme being separated, thereby reducing the ability of the enzyme to act on the substrate.

Upon inclusion of NDSB-195 in the assay system, however, the data became much clearer (black line). In particular, the inclusion of NDSB in this assay shows dramatic improvements in signal over the same system without the zwitterionic component, including a lack of signal in the substrate only control. Further, the effects of the inhibitor also are much more dramatic and clearly evident. The assay was run in continual cycle for six hours with no detectable loss of signal or increase in background fluorescence.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A method of enhancing material transport by electroosmotic flow of a fluid containing said material, comprising:
   providing at least first and second discrete fluid volumes in a fluid filled channel, a first material being contained in said first discrete fluid volume, but not in said second discrete fluid volume; and
   providing an effective concentration of at least one zwitterionic compound in said first discrete volume of fluid containing said first material to reduce an electrophoretic mobility of said first material relative to an electroosmotic flow of said first discrete fluid volume containing said material.

2. The method of claim 1, wherein said effective concentration of said zwitterionic compound in said first discrete volume of fluid is greater than about 5 mM.

3. The method of claim 1, wherein said effective concentration of said zwitterionic compound in said first discrete volume of fluid is from about 5 mM to about 2M.

4. The method of claim 1, wherein said zwitterionic compound is selected from betaine, sulfobetaine, taurine, aminomethanesulfonic acid, a zwitterionic amino acid, HEPES, CAPS, MES, and tricine.

5. The method of claim 4, wherein said zwitterionic compound is a non-detergent sulfobetaine.

6. The method of claim 5, wherein said non-detergent sulfobetaine is selected from dimethylethylaminopropane sulfonic acid, dimethylbenzylaminopropane sulfonic acid, and 3-(N-pyridinium)propane sulfonic acid.

7. The method of claim 1, wherein said first material comprises a plurality of differentially charged chemical species.

8. The method of claim 1, wherein said first material comprises a protein.

9. The method of claim 8, wherein said protein is an enzyme.

10. The method of claim 1, wherein said transport of said discrete fluid volumes is carried out in at least one microscale channel.

11. The method of claim 1, wherein said first discrete volume of fluid containing said material is disposed in a microscale fluidic system which comprises:
    a substrate having at least two intersecting channels disposed therein, at least three ports disposed in said substrate and in fluid communication with free termini of said at least two intersecting channels; and
    a separate electrode placed in electrical contact with each of said ports, whereby a fluid contained in each of said ports is in electrical contact with said electrodes.

12. A method of transporting at least first and second discrete fluid volumes along a fluid filled channel by electroosmosis, the method comprising:
    introducing said first and second discrete fluid volumes into said fluid filled channel, wherein said at least first discrete fluid volume comprises at least a first chemical species having a different net charge than at least a second chemical species contained in said second discrete fluid volume;
    providing an effective concentration of a zwitterionic compound within each of said at least first and second discrete fluid volumes to reduce an electrophoretic mobility of the first and second charged chemical species relative to an electroosmotic mobility of the first and second discrete fluid volumes, respectively; and
    applying a voltage from one point in said channel to a different point in said channel whereby said at least first and second fluid volumes are transported along said fluid filled channel.

13. The method of claim 12, wherein said first and second discrete volumes are transported along said fluid filled channel, substantially without intermixing either of said first or second chemical species.

14. The method of claim 13, wherein each of said at least first and second discrete fluid volumes comprise at least two differentially charged chemical species.

15. The method of claim 14, wherein at least one of said charged chemical species comprises a positively charged chemical species.

16. The method of claim 14, wherein at least one of said charged chemical species comprises a negatively charged chemical species.

17. A microfluidic system comprising:

at least three ports disposed at free termini of at least two intersecting fluid channels, wherein at least one of said channels has at least one cross-sectional dimension of from about 1 $\mu$m to about 500 $\mu$m, and wherein at least one of said channels is capable of propagating free electroosmotic flow of a fluid in said channel;

an electrode placed in electrical contact with each of said ports; and at least first and second discrete volumes of fluid disposed in at least one of said channels, whereby said electrodes present an electric field across said first and second discrete volumes of fluid, and wherein said first and second discrete volumes of fluid comprise an effective concentration of a zwitterionic compound to reduce an electrophoretic mobility of a material contained in said first discrete volume of fluid relative to an electroosmotic flow of said first discrete volume of fluid.

18. The microfluidic system of claim 17, wherein said fluid channels comprise grooves disposed in a surface of a first planar substrate, and a second planar substrate overlays said first planar substrate to form said fluid channels.

19. The microfluidic system of claim 18, wherein at least one of said first and second planar substrates comprise silica.

20. The microfluidic system of claim 17, wherein said system further comprises a fluid direction system which concomitantly and separately modulates a voltage applied at each of at least three of said electrodes.

* * * * *